US00PP07868P

United States Patent [19]

Twomey

[11] Patent Number: Plant 7,868

[45] Date of Patent: May 19, 1992

[54] ROSE PLANT NAMED TWOFREE

[75] Inventor: Jerry Twomey, Leucadid, Calif.

[73] Assignee: DeVor Nurseries, Inc., Watsonville, Calif.

[21] Appl. No.: 611,508

[22] Filed: Nov. 13, 1990

[51] Int. Cl.[5] ..... A01H 5/00
[52] U.S. Cl. ..... Plt./20
[58] Field of Search ..... Plt. 1, 20

[56] References Cited

U.S. PATENT DOCUMENTS

P.P. 3,727 6/1975 Warriner ..... Plt. 20

OTHER PUBLICATIONS

A.R.S., *Modern Roses 8*, The McFarland Company, Harrisburg, Pa. 1980, p. 461.

*Primary Examiner*—James R. Feyrer
*Attorney, Agent, or Firm*—Charles W. Rummler

[57] ABSTRACT

A new and distinct garden and greenhouse rose plant particularly distinguished by its continuous and profuse production of very large flowers having a strong overall Union Jack Red coloration blooming readily from early Spring until late Fall under natural conditions, the flowers being born on long, strong upright stems of a tall plant having a vigorous, upright and sturdy growth habit with abundant foliage.

1 Drawing Sheet

BACKGROUND OF THE NEW PLANT

This new variety of rose plant originated as a seedling hybrid produced by me at my Carlsbad, Calif., nursery, the present hybrid resulting from my crossing of the variety 'Samantha' U.S. Plant Pat. No. 3,727 as a seed parent, with pollen of an unnamed and unpatented seedling selected from my collection of rose plants maintained for breeding purposes. The object of that crossing was to find a plant of good health and vigor, a good production capacity and improved sun resistance and the present seedling was selected from seedlings resulting from the cross because of its solid Red coloration of the flowers and the apparent ability of the plant to meet the aforementioned objectives of the said crossing for the present hybrid. I propagated this selected seedling at the Pleasanton, Calif. nursery of DeVor Nurseries, Inc. by both cuttings and buds and plants so grown in both greenhouse and field clearly demonstrated that the novel characteristics of the selected seedling would be held true from generation to generation and appeared to be firmly fixed and suitable for production on a commercial scale. This new plant was, therefore, set out for commercial scale production at DeVor Nurseries, Inc. at nurseries at Orland, Calif.

DESCRIPTION OF THE DRAWING

My new rose plant is illustrated by the accompanying full color photographic drawing which shows a face view of a fully opened bloom and demonstrates the flower form and the nature of its petals, the color shown being as nearly true to that herein specified as is reasonably possible to obtain by conventional photographic procedures.

DESCRIPTION OF THE NEW VARIETY

The following is a detailed description of my new rose plant based upon observation of plants grown in greenhouse and in the field at Pleasanton, Calif. with color designations being according to the R.H.S. Colour Chart published by The Royal Horticultural Society of London, England.

THE PLANT

Origin: Seedling.
Parentage:
*Seed parent.*—The variety 'Samantha' U.S. Plant Pat. No. 3,727.
*Pollen parent.*—An unnamed and unpatented seedling selected from among rose plants maintained by me for breeding purposes.
Classification:
*Botanic.*—Rosa-hybrid.
*Commercial.*—Garden and Greenhouse Rose.
Form: Upright garden rosebush.
Height: About 100 cm.
Growth habit: Vigorous, upright and very strong.
Foliage: Abundant.
*Number of leaves.*—9 or 10 from last flower cut.
*Shape.*—Odd pinnate.
*Size.*—About 139 mm. long.
*Leaflets.*—Number: 3 and 5. Shape: Oval with denticulate margin. Texture: Semi-Leathery. Aspect: Smooth and glossy. Color: Upper side — Yellow Green 147-A. Under side — Yellow Green 147-B.
*Stipules.*—Adnate.
*Rachis.*—72 mm. on 3 part leaf and 139 mm. on 5 part leaf.
*Petioles.*—Length: About 8 or 9 mm. on 3 part leaf and about 16 mm. on 5 part leaf.
Ribs and veins: Depressed on top of leaf and slightly rounded on bottom side of leaf.
Thorns: Declining and 7 to 10 mm. long.
*Color.*—Greyed Purple 187-B.

THE BUD

Size: Small.
*Diameter.*—About 17 mm.
*Length.*—About 22 mm.
Shape: Ovoid and pointed.
Rate of opening: Slow.
Color of petals:

*When sepals first divide.*—Red 45-A.

*When petals begin to unfurl.*—Red 45-B.

Sepals:

*Number.*—5.

*Shape.*—Spreading with leaf-pointed ends.

*Character.*—Hooded over the bud and curled back when flowers open.

*Color.*—Inside — Yellow Green 148-C. Outside — Yellow Green 144-B with tinges of Greyed Orange 176-C spotted throughout.

Calyx:

*Shape.*—Funnel-shaped.

*Size.*—Medium. Width: About 10 mm. Length: About 8 mm.

*Splitting.*—Calyx does not split.

*Aspect.*—Smooth.

Peduncle of flower stem:

*Length.*—About 49 to 55 mm.

*Character.*—Rigid, erect and sturdy.

*Color.*—Yellow Green 146-B.

THE FLOWER

Blooming habit: Continuous and profusely from early Spring through Summer and Fall, and blooming freely under natural conditions during Fall.

Size of bloom: Medium.

*Diameter.*—About 69 to 72 mm.

*Depth.*—About 33 mm.

Borne: Singly on strong, upright stems.

Shape:

*When bloom first opens.*—Slightly high centered.

*When bloom matures.*—Cupped imbricated.

Petalage:

*Number.*—33.

*Arrangement.*—Very nicely imbricated.

*Form.*—Spoon shaped and imbricated with ruffled margins and acute apex.

*Texture.*—Semi-leathery and soft.

*Aspect.*—Velvety.

*Color.*—All petals — Red 45-B with Yellow base 4-D surrounded by Green Yellow 1-D. Reverse side: Body and margin — 53-B.

*Petaloids.*—Number: 4. Color: Red 45-A with Yellow White base 158-D.

Peduncle of flower stem:

*Length.*—49 to 55 mm.

*Strength.*—Sturdy.

Discoloration after full bloom: None.

Persistence: The flower will hang on and dry.

Disease resistance: Very resistant to mildew, rust and black spots as observed at Watsonville, Calif.

Fragrance: Mild musk.

Lasting quality: Long lasting on the plant and as a cut flower.

THE REPRODUCTIVE ORGANS

Stamens:

*Number.*—132.

*Arrangement.*—Introrse.

*Anthers.*—Size: 4 mm. Color: Yellow Orange 22-A.

*Filaments.*—Length: About 9 mm. Color: Red 54-B and fading into Green White 157-D.

*Pollen.*—Color: Yellow Orange 22-A around lip with tinges of Red 54-B.

Pistils:

*Number.*—93.

*Styles.*—Length: About 10 to 12 mm. Color: Green White 157-D to Red 57-C at the top.

*Stigmas.*—Color: Yellow 9-D.

Character of the ovaries: Small, flattened and oblong with Whitish covering of silvery hairs.

THE FRUIT

Fertility: The fruit is fertile.

I claim:

1. The new and distinct rose variety substantially as herein shown and described, characterized by its continuous and profuse production of medium sized blossoms having a solid Union Jack Red color on all of its petals; the plant having a vigorous, upright and free branching growth habit with abundant foliage.

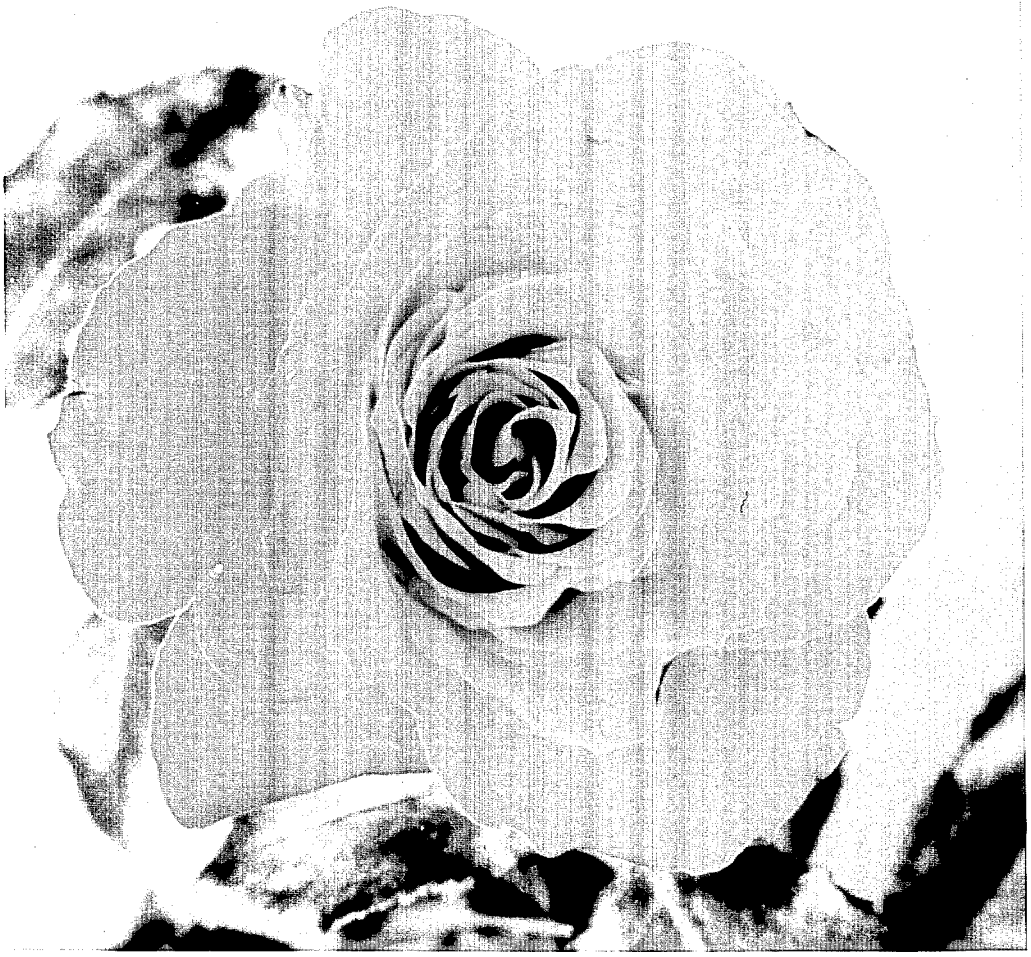

* * * * *